(12) United States Patent
Lechmann et al.

(10) Patent No.: US 8,182,536 B2
(45) Date of Patent: May 22, 2012

(54) TOTAL DISC REPLACEMENT DEVICE

(75) Inventors: Beat Lechmann, Grenchen (CH); Gregor Feigenwinter, Lampenberg (CH); Roger Buerki, Chur (CH)

(73) Assignee: Synthes USA, LLC, West Chester, PA (US)

( * ) Notice: Subject to any disclaimer, the term of this patent is extended or adjusted under 35 U.S.C. 154(b) by 412 days.

(21) Appl. No.: 11/719,355

(22) PCT Filed: Feb. 1, 2006

(86) PCT No.: PCT/CH2006/000064
§ 371 (c)(1),
(2), (4) Date: Apr. 24, 2009

(87) PCT Pub. No.: WO2007/087730
PCT Pub. Date: Aug. 9, 2007

(65) Prior Publication Data
US 2010/0036497 A1      Feb. 11, 2010

(51) Int. Cl.
*A61F 2/44* (2006.01)
(52) U.S. Cl. .................................. 623/17.16
(58) Field of Classification Search .... 623/17.11–17.16; 606/246, 249, 257
See application file for complete search history.

(56) References Cited

U.S. PATENT DOCUMENTS

| | | | |
|---|---|---|---|
| 7,637,955 B2 * | 12/2009 | Marik et al. | 623/17.14 |
| 7,842,089 B2 * | 11/2010 | Aaron | 623/17.16 |
| 2002/0082701 A1 | 6/2002 | Zdeblick et al. | |
| 2004/0193273 A1 * | 9/2004 | Huang | 623/17.12 |
| 2005/0154468 A1 | 7/2005 | Rivin | |
| 2006/0190084 A1 * | 8/2006 | Doubler et al. | 623/17.14 |
| 2006/0229724 A1 * | 10/2006 | Lechmann et al. | 623/17.11 |
| 2006/0229725 A1 * | 10/2006 | Lechmann et al. | 623/17.11 |

(Continued)

FOREIGN PATENT DOCUMENTS

EP      0 950 389 A2      10/1999

(Continued)

OTHER PUBLICATIONS

Meakin, Judith R. et al., "Replacing the nucleus pulposus of the intervertebral disc," Clinical Biomechanics 16 (2001), 560-565.*

(Continued)

*Primary Examiner* — Eduardo C Robert
*Assistant Examiner* — Mary Hoffman
(74) *Attorney, Agent, or Firm* — Stradley Ronon Stevens & Young, LLP

(57) ABSTRACT

An intervertebral implant for implantation between an upper vertebra and a lower vertebra having a central axis. The implant may have a first member with a top surface for contacting at least a portion of the upper vertebra and a bottom surface as well as a second member with a top surface and a bottom surface for contacting at least a portion of the lower vertebra. An elastic spacer may be disposed between the first member and the second member. The bottom surface of the first member and the top surface of the second member may have a first constraint means and the other of the bottom surface of the first member and the top surface of the second member may be provided with a second constraint means, to limit the amount of lateral movement between the first and second members. Additionally, the constraint means may be sized and configured such that a gap with a width greater than zero is provided at least transversely to the central axis between the first and second constraint means in an unloaded state.

25 Claims, 5 Drawing Sheets

U.S. PATENT DOCUMENTS

| | | | |
|---|---|---|---|
| 2006/0265068 A1* | 11/2006 | Schwab | 623/17.11 |
| 2007/0067036 A1* | 3/2007 | Hudgins et al. | 623/17.13 |
| 2007/0276495 A1* | 11/2007 | Aaron | 623/17.12 |

FOREIGN PATENT DOCUMENTS

| | | |
|---|---|---|
| EP | 1 214 918 A1 | 6/2002 |
| EP | 1 532 950 A1 | 5/2005 |
| FR | 2 787 021 A1 | 6/2000 |
| FR | 2 863 868 A1 | 6/2005 |
| WO | 2005/084385 | 9/2005 |

OTHER PUBLICATIONS

"X10Cr13 Stainless Steel for medical instruments Specification Sheet," Matweb, p. 1.*
"Titanium Allots, General Specification Sheet," Matweb, p. 1.*
Search Report for PCT/CH2006/000064 (Oct. 20, 2006).
International Search Report and Written Opinion of the International Searching Authority for International Application No. PCT/CH2006/000064 dated Oct. 20, 2006.

* cited by examiner

TOTAL DISC REPLACEMENT DEVICE

FIELD OF THE INVENTION

The invention relates to a total disc replacement device to be used as a replacement of an intervertebral disc.

DESCRIPTION OF THE PRIOR ART

Currently, degenerated intervertebral discs are treated with fusion cages for arthrodesis and lower grade degenerated discs are replaced by arthroplasty devices. These devices contain mechanical elements including an articulating portion, e.g. a ball-and-socket-joint. Such devices shall mimic the segmental motion pattern. However, the natural motion pattern of two adjoining vertebral bodies is very complex due to the surrounding structures which provide mechanical stabilization. Facet joints, remaining ligaments or residual fragments of the annulus fibrosis are part of the segmental stabilization.

For the currently available Total Disc Replacement Implants the surgeon shall remove the Anterior Longitudinal Ligament (ALL) and the Posterior Longitudinal Ligament (PLL) in order to release the motion segment completely. After such a surgical intervention, the total disc replacement implant can provide the function as a prosthesis.

An artificial disc implant is known from US-A 2002/0082701 ZDEBLICK. This U.S. patent application discloses an artificial disc implant which is provided with an upper and a lower shell as well as an elastic spacer therebetween. Furthermore, the surfaces of the shells which are facing each other are provided with constraint means by means of which the motion of the shells relative to one another is limited. Nevertheless, the disclosed configuration of the constraint means does not allow a rigid limitation of the lateral motion of the shells relative to one another until the implant is completely compressed.

An intervertebral disc prosthesis is known from EP-A 1 532 950 FILIPPI. This known prosthesis is provided with two apposition members separated by a lens shaped core. The core has two opposite spherical articulating surfaces which slidably engage corresponding recesses in the intermediate surfaces of the apposition members. Furthermore, the core is provided with bores penetrating into the core at the vertices of the articulating surfaces wherein each a pin attached to the intermediate surface is receivable in a laterally displaceable manner. The pin being laterally displaceably arranged in the bore together with the lateral wall of the bore serve as constraint means but since the second constraint means are configured at the elastic core said constraint means do not allow to rigidly limit the lateral motion and the pivoting of the two apposition members relative to one another within a desired range.

An implantable intervertebral disc prosthesis having a pair of opposed shell like apposition members and a resilient central body disposed between these apposition members is known from US-A 2003/0135277 BRYAN. This known disc prosthesis comprises constraint means which limit the range of lateral bending and lateral translation of the two apposition members relative to each other and consequently of the adjacent vertebral bodies relative to each other. Disadvantageously, the inner constraint means are arranged at the resilient central body and do therefore not allow a rigid limitation of the range of motion.

Accordingly, it is the principal object of the present invention to provide a total disc replacement device which permits a dampened motion of the apposition members relative to each other until a rigid limitation of the range of at least the lateral motion is reached.

According to the invention the above object is achieved through a total disc replacement device with a central axis and comprising a first apposition member with an apposition surface and an intermediate surface both being arranged transversely to said central axis and a second apposition member with an apposition surface and an intermediate surface; said intermediate surfaces of said first and second apposition members facing each other. Furthermore, an elastic spacer disposed between said intermediate surfaces of said first and second apposition members is provided. Said intermediate surface of said first apposition member is provided with first rigid constraint means and said intermediate surface of said second apposition member is provided with second rigid constraint means interfering with said first constraint means and being configured such that a gap with a width W>0 is provided at least transversely to the central axis between said first and second constraint means in the unloaded state of the total disc replacement device.

The device according to the invention as such offers the advantages that:

(a) the translation in lateral or in antero-posterior direction of the adjacent vertebral bodies relative to each other is limited, particularly in case of extreme bending of the vertebra;

(b) the facet joints are protected in case of lateral or antero-posterior movement as well as in case of axial rotation of the spinal segment of the adjacent vertebral bodies;

(c) the motion of the adjacent vertebral bodies is dampened due to the elastic property of the spacer between the rigid metallic apposition members;

(d) the more the elastic spacer is compressed, the more it acts as a soft break;

(e) the total disc replacement device is apt to restore the lordotic curve and distract the segment due to the combined rigid-elastic structure of the device;

(f) a superposed motion of the total disc replacement device is allowed similar to the natural intervertebral disc.

In a preferred embodiment said spacer extends into the gap between the first and second constraint means, thus allowing the advantage of a damping effect in case of relative motion of the first and second apposition members.

In a further embodiment said spacer completely fills the gap.

In yet a further embodiment said first and second constraint means are configured to limit the displacability of said first and second apposition member relative to one another at least transversely to said central axis, thus allowing a rigid limitation of the range of motion of said first and second apposition member as such of the adjoining vertebral relative to one another.

In another embodiment said elastic spacer is made of a material A having a Young's modulus $Y_A$ and said first and second apposition members are made of a material B having a Young's modulus $Y_B$ and wherein $Y_A$ is between 4% and 66% of $Y_B$.

In a further embodiment the Young's modulus $Y_A$ of said material A is smaller than 60 GPa.

In yet another embodiment the Young's modulus $Y_A$ of said material A is between 15 GPa and 60 GPa.

In still a further embodiment the Young's modulus $Y_B$ of said material B is greater than 90 GPa.

In again another embodiment the Young's modulus $Y_B$ of said material B is between 90 GPa and 350 GPa.

In a further embodiment said elastic spacer is made of a composite material or a material combination, thus allowing the advantage that e.g. two different polymeric materials permit a more sophisticated damping effect.

In yet a further embodiment the first and second apposition plate are made from a metal, preferably titan or a titan alloy.

In another embodiment the elastic spacer is made from a plastic.

In still a further embodiment said first or second constraint means comprises a projection protruding over the respective intermediate surface and the other of said first and second constraint means comprises at least one limiting wall axially overlapping said projection.

In yet another embodiment said at least one limiting wall is configured to permit a displacement of said projection within an area orthogonal to said central axis.

In a further embodiment said first and second constraint means are located centrally on said intermediate surfaces.

In yet a further embodiment the constraint means are configured in a manner that:

the projection has a diameter between 1.5 mm and 18 mm;

the at least one limiting wall limits the motion of the projection within a length l between 2 mm and 24 mm measured parallel to the first transverse axis which preferably coincides or is parallel to the lateral axis of the vertebral bodies; and within a width b between 1.8 mm and 32 mm measured parallel to the second transverse axis which preferably coincides or is parallel with the antero-posterior axis of the vertebral bodies.

In a further embodiment said gap has a width W1 parallel to a first transverse axis being orthogonal to the central axis and a width W2≠W1 parallel to a second transverse axis being orthogonal to the central axis and the first transverse axis. This design allows the advantage that the motions of the first and second apposition plate relative to one another in the antero-posterior direction and in the lateral direction are differently limited through the constraint means.

In another embodiment said first constraint means is configured as a central pin protruding over said intermediate surface of said first apposition member.

In yet a further embodiment said central pin has a convex, preferably spherical tip allowing a tilting motion between the first and second apposition member when the elastic spacer is compressed parallel to the central axis until the intermediate surface of the second apposition member abuts the tip of the central pin. The advantage of this design is a limitation of the elastic compressibility of the implant parallel to the central axis.

In still another embodiment said second constraint means are formed by at least one curved protrusion projecting out over said intermediate surface of said second apposition member, thus allowing the advantage of a configuration which provides more constrain, i.e. less translation in antero-posterior direction whereas it allows more motion laterally. This configuration has its advantages by the treatment of Spondylo-listhesis grade 1 according to Meyerding. This slight misalignment can be treated with total disc replacement implant without additional stabilization.

In a further embodiment said at least one curved protrusion is provided with a concavely curved interior wall facing the central axis which forms a boundary line of the cross-sectional area of the at least one protrusion orthogonal to the central axis, said boundary line being at least a section of a circle, an oval or an ellipse.

In another embodiment said second constraint means comprises two curved protrusions having cross-sectional areas orthogonal to the central axis that are centrally symmetric to the point of intersection where the central axis cuts the intermediate surface of said second apposition member.

In yet a further embodiment said first and second constraint means comprise a keel and a groove being in tiltable engagement.

In another embodiment said first and second constraint means comprise a spherical segment and a corresponding spherical recess.

In a further embodiment said total disc replacement device additionally comprises form fitting retention means disposed between said first and second apposition members and said elastic spacer, thus allowing the advantage of a rigid bonding of the elastic spacer to the first and second apposition plates.

In another embodiment said retention means comprise a peripheral frame projecting out over said intermediate surfaces of said first and second apposition members, said peripheral frame being provided with an undercut and being encompassed by said elastic spacer.

In still a further embodiment said intermediate surfaces of said first and second apposition members contact said elastic spacer over the entire area of said intermediate surfaces, and said first and second apposition members and said elastic spacer form a compact body with planar or convex lateral surfaces. This design allows the advantage of preventing fluid from the human body flowing into the implant and destroy the implant.

In yet a further embodiment said first and second apposition members have an elongated shape with a major axis and a transverse minor axis when viewed parallel to said central axis.

In another embodiment said first and second apposition members have a length L measured parallel to said major axis and a maximum width B measured parallel to said transverse minor axis, whereby the ratio of the length L to the maximum width B is between 3:1 and 5:1. This embodiment offers the advantage that it is only necessary to clear a narrow access path such permitting an extraforaminal approach to the intervertebral disc space.

In a further embodiment said central axis, major axis and transverse minor axis intersect each other and said central axis and transverse minor axis define a middle plane and whereby said first and second apposition members have a cross-sectional area orthogonal to said central axis which is essentially oval or elliptical and comprises at least two concavities lying on different sides of said middle plane and on the same side of said major axis. The advantages of this design essentially are:

unnecessary material on the first and second apposition plates (bone contact plates) is removed in order to give special attention to the fact that the bony endplates of the vertebral bodies change their shape at the location where the prosthesis is situated during their degeneration, i.e. they become more undulated over time; and possible osteophytes on the posterior periphery of the vertebral endplates which the surgeon decides not to remove are taken into consideration, i.e. the intervertebral prosthesis can be positioned easier because the prosthesis can be manipulated around the undulations.

In yet another embodiment said cross-sectional area of said first and second apposition members is kidney shaped with an enlargement arranged essentially symmetrical to said middle plane.

In still a further embodiment said at least two concavities have an essentially semi-elliptical or semi-oval shape.

In another embodiment said at least two concavities are disposed essentially symmetrical to said middle plane.

In yet a further embodiment said first and second apposition members have a length L measured parallel to said major axis and wherein each of said at least two concavities has a width W measured parallel to said major axis, said width W amounting to between 15% and 35% of said length L.

In still another embodiment said first and second apposition members have a maximum width B measured parallel to said transverse minor axis and wherein each of said at least two concavities has a depth T measured parallel to said transverse minor axis, said depth T amounting to between 3% and 25% of said maximum width B.

In a further embodiment said cross-sectional area of said first and second apposition members has an essentially elliptical periphery with a smaller radius of curvature at the first subsidiary vertex than at the second subsidiary vertex of said periphery.

In yet another embodiment said first subsidiary vertex is on the same side of said major axis as said at least two concavities.

In still a further embodiment said spacer completely fills the gap.

In another embodiment said first and second constraint means are configured to permit a relative displacement of said first and second apposition members parallel to said central axis.

In yet another embodiment said first and second constraint means interfere mechanically.

Brief description of the surgical implantation methods:
Variant I: (FIGS. 1-3)
This type of total disc replacement device is implanted from anterior, anterolateral or lateral applying known surgical techniques.

Variant II: (FIGS. 4 and 5)
This type of total disc replacement device is implanted as an interbody fusion cage. Since one crucial aspect of the implantation of a total disc replacement device is to keep the anterior longitudinal ligament (ALL) and the posterior longitudinal ligament (PLL) intact, preferably posteriorly inserted total disc replacement devices are designed which are—due to the small access to the intervertebral space—applied in pairs. The above mentioned ligaments and the residual elements of the annulus fibrosis provide segmental stability to the functional spine unit or spinal motion segment. The two devices are inserted through a posterior median incision whereby the devices have to pass the spinal canal.

Variant III: (FIGS. 6-8)
The device is inserted into the intervertebral space by means of an extraforaminal access.

A BRIEF DESCRIPTION OF THE DRAWINGS

Further objects and advantages of the invention will become apparent from the following description when read with reference to the accompanying drawings which illustrate several embodiments of the invention. In the drawings.

DETAILED DESCRIPTION

Figure 1:
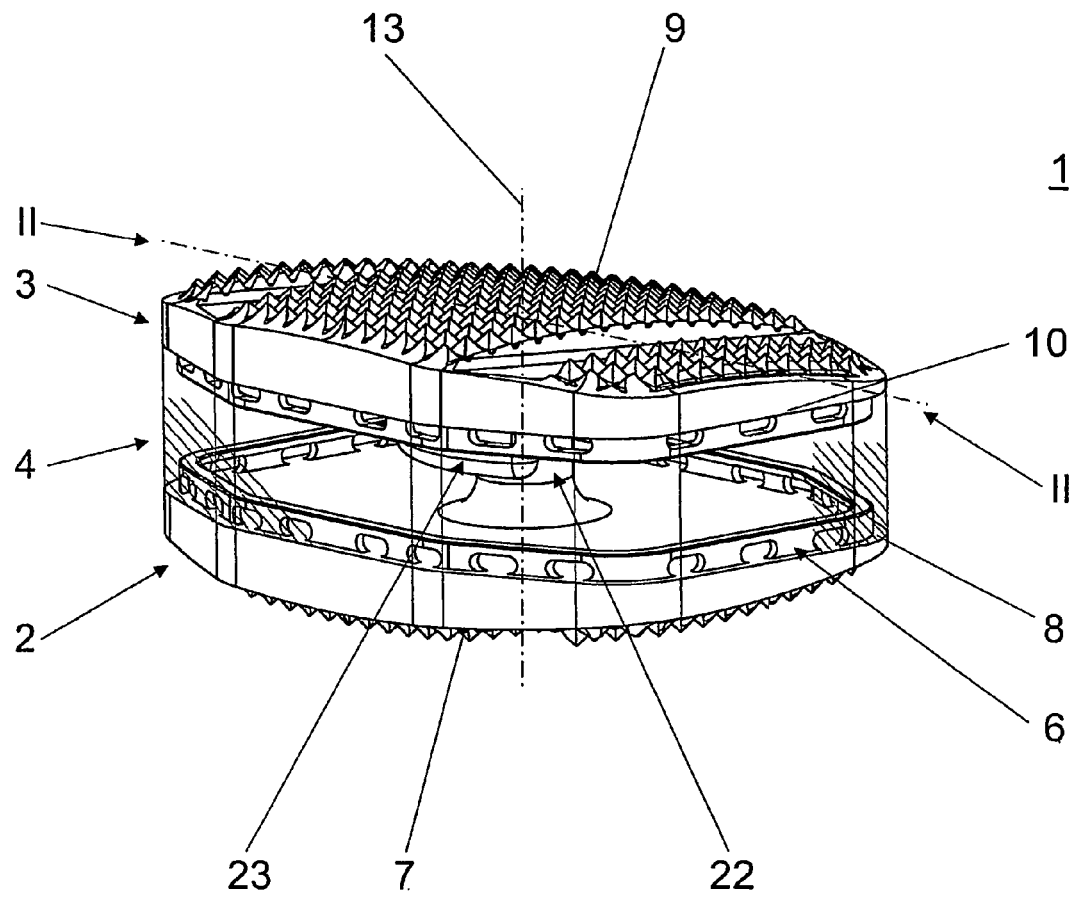
FIG. 1 shows a perspective view of an embodiment of a total disc replacement device according to the present invention.

In FIG. 1 an embodiment of a total disc replacement device 1 according to the invention is represented which comprises a first and a second plate-shaped apposition member 2;3 and an elastic spacer 4 disposed between the first and second apposition member 2;3. The first and second apposition members 2;3 and the elastic spacer 4 are being cut by a central axis 13 extending along the longitudinal axis of the vertebra. The first and second apposition members 2;3 each comprise an apposition surface 7;9 and an intermediate 8;10 whereby said apposition surfaces 7;9 are apt to abut the end plates of the adjoining vertebral bodies and whereby said intermediate surfaces 8;10 are arranged facing each other. Furthermore, the elastic spacer 4 comprises a first and a second surface which are essentially parallel and abut an intermediate surface 8; 10 of the apposition members 2;3 each. In order to limit the mutual translation of the apposition members 2;3 transverse to the central axis 13 the intermediate surfaces 8; 10 of the first and second apposition members 2;3 are provided with first and second constraint means 22;23.

The first constraint means 22 is provided at the intermediate surface 8 of said first apposition member 2 while the second constraint means 23 is provided at the intermediate surface 10 of said second apposition member 3 in a manner that said second rigid constraint means 23 interfere with said first constraint means 22 and being configured such that a gap 21 is provided transversely as well as parallel to the central axis 13 between said first and second constraint means 22;23 in the unloaded state of the total disc replacement device 1. The elastic spacer 4 completely fills the gap 21 such allowing a damping effect in case of relative motion of said first and second apposition member 2; 3 in three orthogonal directions.

Figure 2:
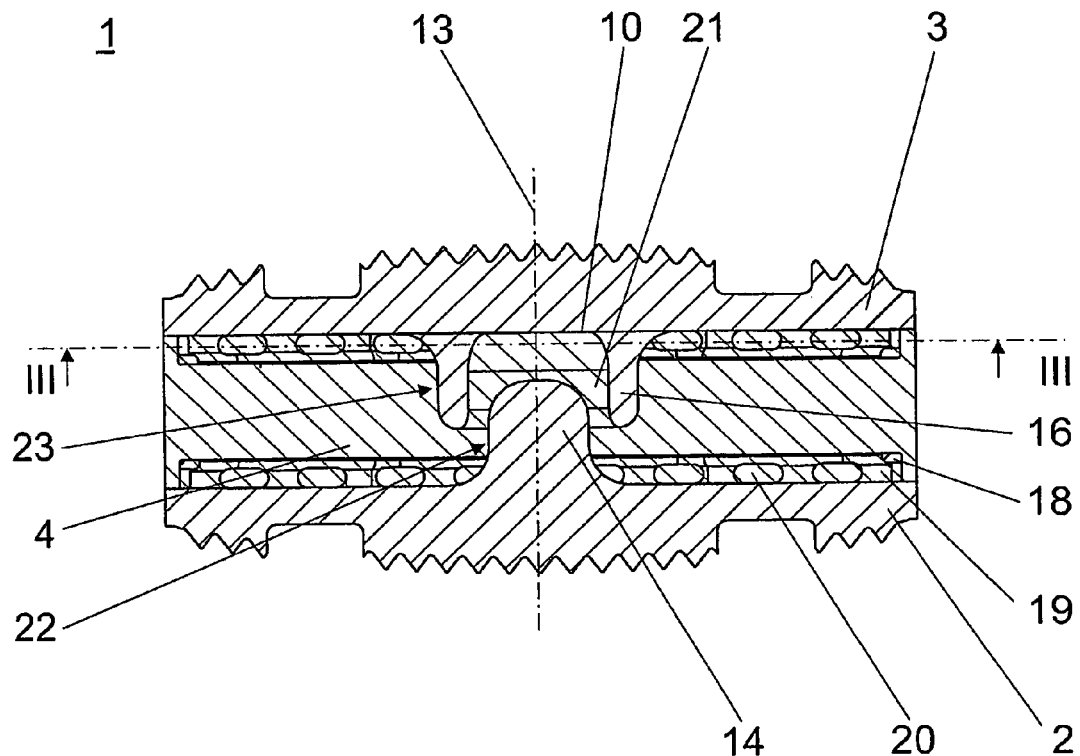
FIG. 2 shows a cross-section through the device of FIG. 1 along the line II-II.
Figure 3:
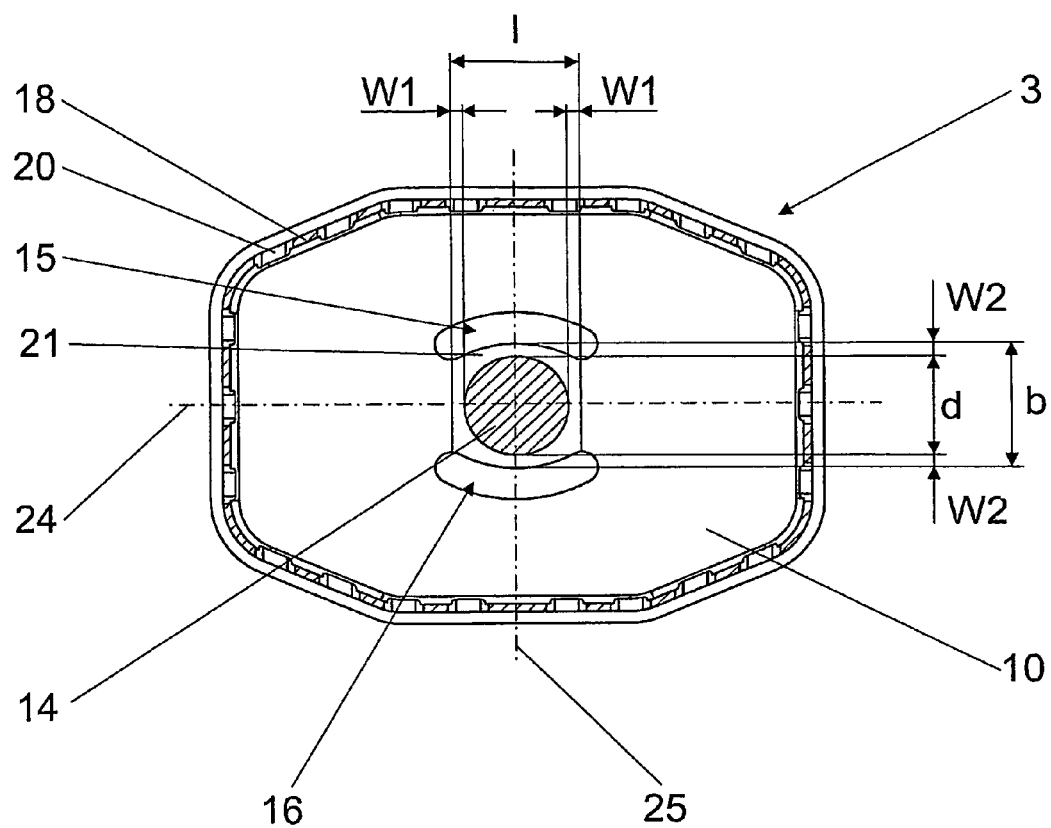
FIG. 3 shows a cross-section through the device of FIGS. 1 and 2 along the line III-III in FIG. 2.

As shown in FIGS. 2 and 3 the first constraint means 22 are configured as a projection having the form of a central pin 14 protruding over the intermediate surface 8 of the first apposition member 2 while the second constraint means 23 comprise first and second curved protrusions 15; 16 at the intermediate surface 10 of the second apposition member 3, said first and second curved protrusions 15; 16 enclosing a recess partially surrounding said central pin 14 such forming a rigid spatial limitation. The central pivot pin 14 has a certain range of motion parallel and transverse to the central axis 13 within said spatial limitation.

As shown in FIG. 3 said gap 21 has a width W1 parallel to a first transverse axis 24 being orthogonal to the central axis 13 and a width W2≠W1 parallel to a second transverse axis 25 being orthogonal to the central axis 13 and the first transverse axis 24 such allowing relative motions of the first and second apposition member 2; 3 being differently in the antero-posterior direction and in the lateral direction.

Furthermore, said central pin 14 has a convex tip further allowing a tilting motion between said first and second apposition member 2;3 when the elastic spacer 4 is compressed parallel to the central axis 13 until the intermediate surface 10 of the second apposition member 3 abuts the tip of the central pin 14.

Said first and second curved protrusion 15;16 being provided with a concavely curved interior wall facing the central axis 13 which forms a boundary line of the cross-sectional area of each of said first and second protrusion 15;16 orthogonal to the central axis 13, said boundary line being a section of an ellipse. Furthermore, said first and second curved protrusions 15;16 have a cross-sectional area orthogonal to the central axis 13 such that the two cross-sectional areas are centrally symmetric to the point of intersection where the central axis 13 cuts the intermediate surface 10 of said second apposition member (3).

Furthermore, said total disc replacement device 1 comprises form fitting retention means 6 disposed between each of said first and second apposition members 2;3 and said elastic spacer 6 such allowing a firm bonding of the elastic spacer 4 to the first and second apposition plates 2;3. Said retention means 6 consist of a peripheral frame 18 disposed near the periphery of the cross-sectional areas orthogonal to said central axis 13 of said first and second apposition member 2;3 and projecting out over said intermediate surfaces 8;10 of said first and second apposition members 2;3. An undercut 19 is provided at said peripheral frame 18 which is encompassed by said elastic spacer 4. Furthermore, said peripheral frame 18 is provided with perforations 20 penetrating the peripheral frame 18 transversely to said central axis 13 and being filled with the material of said elastic spacer 4.

Figure 4:
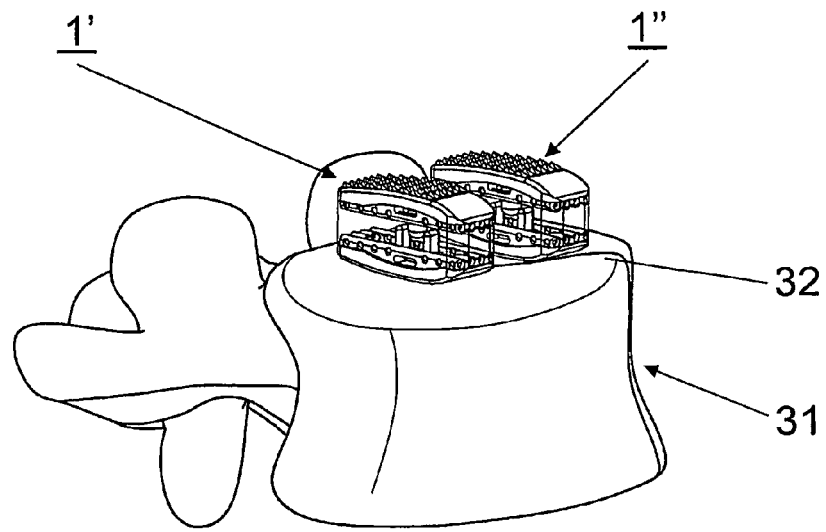
FIG. 4 shows a perspective view of a vertebral body whereby the intervertebral space adjoining its cover plate is being provided with two other embodiments of total disc replacement devices according to the present invention.
Figure 5:
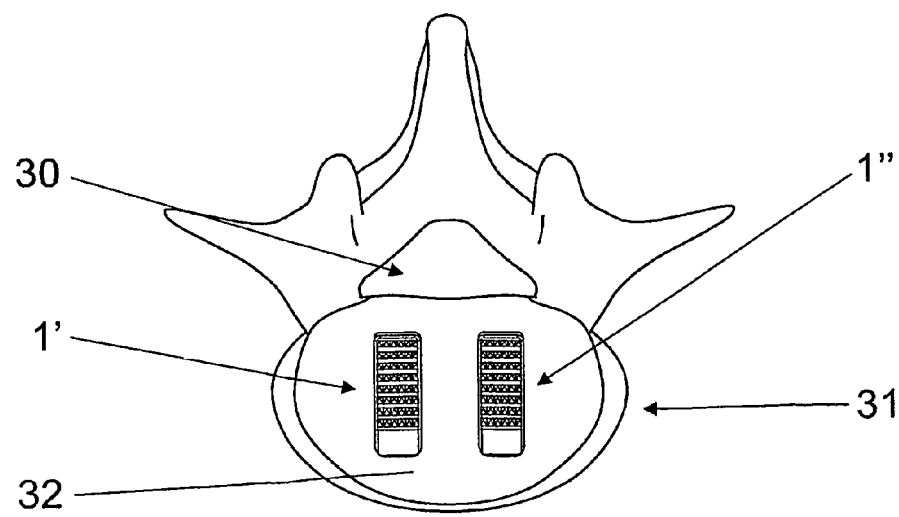
FIG. 5 shows a top view on the vertebral body of FIG. 4.

FIGS. 4 and 5 show posteriorly inserted total disc replacement devices 1'; 1" that are both provided with constraint means 22; 23 and form fitting retaining means 6 as illustrated in FIGS. 1-3. The total disc replacement devices 1'; 1" therefore essentially differ only in their lateral and antero-posterior dimensions from the total disc replacement device 1 shown in FIGS. 1-3. Due to the small access to the intervertebral space these lateral and antero-lateral dimensions must be selected such that the total disc replacement devices 1'; 1" must be implanted in pairs. Since one crucial aspect to apply the surgical techniques as described above are the intact anterior longitudinal ligaments and the posterior longitudinal ligaments. These ligaments and the residual elements of the annulus fibrosis provide segmental stability to the functional spine unit or spinal motion segment. From posterior lumbar interbody fusion surgery it is known that all these structures remain intact. Therefore, posteriorly inserted total disc replacement devices 1'; 1" can be designed and applied with motion preserving elements, i.e. an elastic spacer 4 as well. Said pair of total disc replacement devices 1'; 1" are inserted through the posterior median incision as described above under variant 2. The devices must be passed through the spinal canal during insertion. Furthermore, the elastic spacer 4 allows even a slight malpositioning of the total disc replacement devices 1'; 1" since there are no predefined centers of rotation as being provided by implants having e.g. a spherical ball-and-socket joint.

Figure 6:
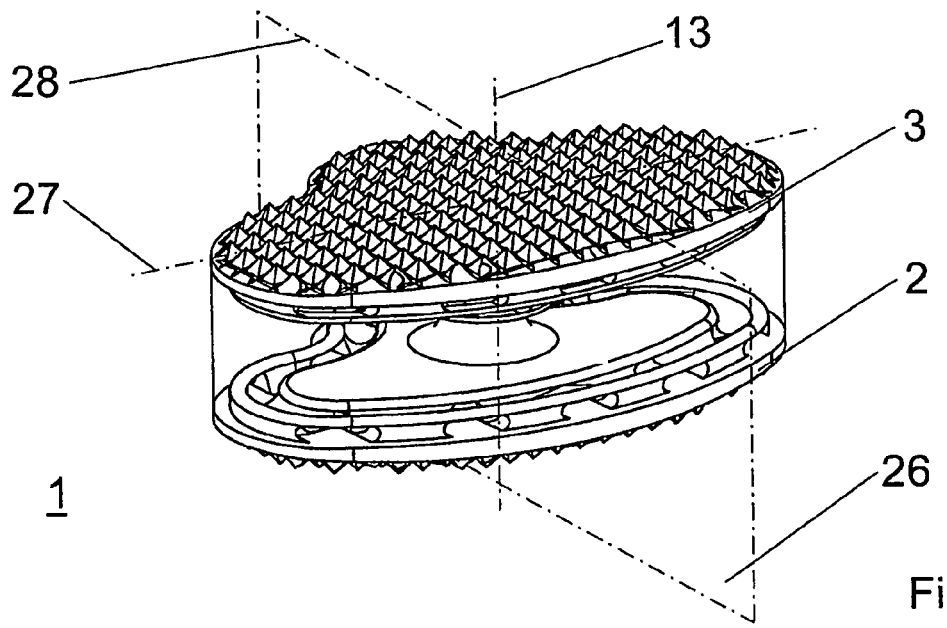
FIG. 6 shows a perspective view of another embodiment of a total disc replacement device according to the present invention.
Figure 7:
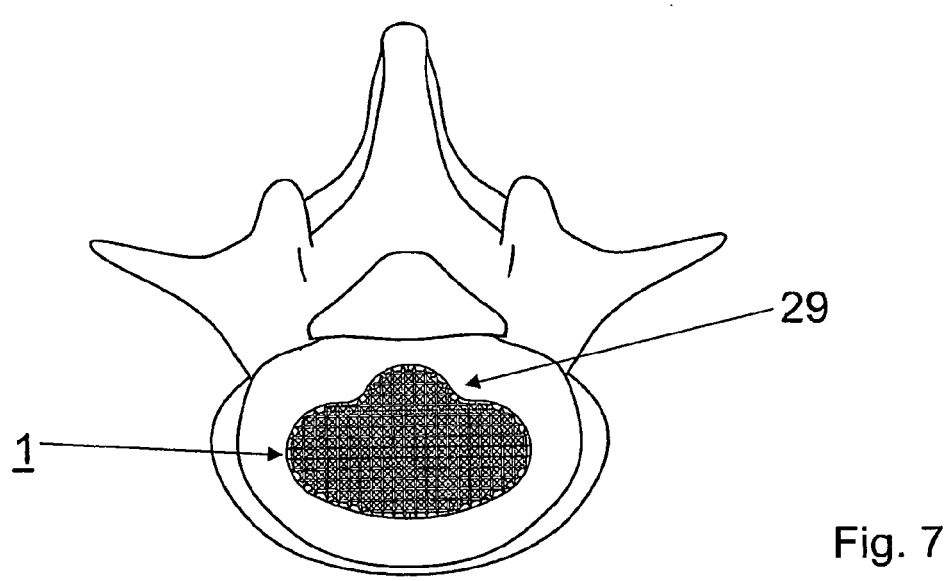
FIG. 7 shows a top view of a vertebral body whereby the intervertebral space adjoining its cover plate is being provided with the device of FIG. 6.
Figure 8:
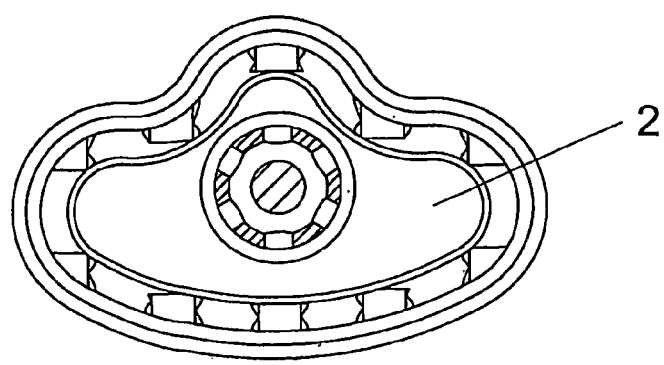
FIG. 8 shows a top view on the second apposition member of the device of FIGS. 6 and 7.

The embodiment shown in FIGS. 6-8 differs from the embodiment shown in FIGS. 1-3 only in the shape of the cross-sectional area orthogonal to said central axis 13 of the first and apposition member 2; 3. FIGS. 6-8 illustrate an embodiment also comprising a first apposition member 2, a second apposition member 3 and an elastic spacer 4 therebetween. Opposite said elastic spacer 4 the first and second apposition member 2; 3 comprise a first apposition surface 7, respectively a second apposition surface 9, whereby said second apposition surface 9 is configured for abutting the base plate of a first intervertebral body contacting the total disc replacement device 1 on top and said first apposition surface 7 is configured for abutting the cover plate of a second intervertebral body contacting the total disc replacement device 1 at the bottom.

Each of the first and second apposition surfaces 7; 9 is disposed transversely to the central axis 13. When viewed parallel to said central axis 13 said first and second apposition members 2; 3 have an elongated shape with a major axis 27 and a transverse minor axis 28, whereby said central axis 13, major axis 27 and transverse minor axis 28 intersect each other. Said central axis 13 and said transverse minor axis 28 further define a middle plane 26. Furthermore, said first and second apposition member 2; 3 have a cross-sectional area orthogonal to said central axis 13 which is essentially elliptical and comprises two concavities lying on different sides of said middle plane 26 and on the same side of said major axis 27.

The two concavities are disposed symmetrically to said middle plane 26 such that one of said two concavities is arranged in a first quadrant of a circle the centre of which coincides with the point of intersection of the major axis 27, the transverse minor axis 28 and the central axis 13 and the circumference of which is tangent to the periphery of said cross-sectional area at the principal vertices. The second of said two concavities is arranged in a clockwise succeeding, second quadrant of said circle. Furthermore, the two concavities have an essentially semi-elliptical shape and have a depth T measured parallel to said transverse minor axis 28 amounting to about 5% of the maximum width B of said first and second apposition members 2; 3.

What is claimed is:

1. An intervertebral implant for implantation between an upper vertebra and a lower vertebra, the intervertebral implant having a central axis and comprising:
    a first member with a top surface for contacting at least a portion of the upper vertebra and a bottom surface, the first member having a peripheral edge;
    a second member with a top surface and a bottom surface for contacting at least a portion of the lower vertebra, the second member having a peripheral edge;
    an elastomeric material disposed between said bottom surface of said first member and said top surface of said second member, the elastomeric material is a single continuous material extending from and between the peripheral edges of the first and second members and the bottom surface of the first member and the top surface of the second member;
    wherein one of said bottom surface of said first member and said top surface of said second member is provided with first constraint means and the other of said bottom surface of said first member and said top surface of said second member is provided with second constraint means, said first and second constraint means being sized and configured to limit the amount of lateral movement between said first and second members;
    wherein said first and second constraint means are sized and configured such that a gap with a width greater than zero is provided at least transversely to said central axis between said first and second constraint means in an unloaded state;
    wherein said first constraint means is configured as a central pin, said central pin having a width and a convex tip for permitting a tilting motion between said first and second members; and wherein the second constraint means comprises two separate curved concave protrusions surrounding the first constraint means, the two separate concave protrusions defining two opposite openings, the openings being smaller than the width of the central pin, wherein the two opposite openings allow relative movement of the first and second members in the antero-posterior direction to differ from the amount of relative movement in the lateral direction.

2. The intervertebral implant of claim 1, wherein said elastomeric material extends into said gap.

3. The intervertebral implant of claim 1, wherein said first constraint means is located centrally on one of said bottom surface of said first member and said top surface of said second member and said second constraint means is located centrally the other of said bottom surface of said first member and said top surface of said second member.

4. The intervertebral implant of claim 1, wherein said elastomeric material is made of a material A having a Young's modulus YA and said first and second members are made of a material B having a Young's modulus YB and wherein YA is between 4% and 66% of YB.

5. The intervertebral implant of claim 4, wherein the Young's modulus YA of said material A is smaller than 60 GPa.

6. The intervertebral implant of claim 5, wherein the Young's modulus YA of said material A is between 15 GPa and 60 GPa.

7. The intervertebral implant of claim 4, wherein the Young's modulus YB of said material B is greater than 90 GPa.

8. The intervertebral implant of claim 7, wherein the Young's modulus YB of said material B is between 90 GPa and 350 GPa.

9. The intervertebral implant of claim 1, wherein said gap has a width W1 parallel to a first transverse axis orthogonal to said central axis and a width W2 parallel to a second transverse axis orthogonal to said central axis and said first transverse axis, said width W1 being different from said width W2.

10. The intervertebral implant of claim 1, wherein said first and second curved protrusions each include a concavely curved interior wall face.

11. The intervertebral implant of claim 1, further comprising form fitting retention means disposed between said first member and said elastomeric material, and disposed between said second member and said elastomeric material, said retention means comprising a peripheral frame extending from said bottom surface of said first member and said top surface of said second member, said peripheral frame being sized and configured to secure said elastomeric material in-between said first and second members.

12. The intervertebral implant of claim 11, wherein said peripheral frame includes an undercut, the undercut being sized and configured to be encompassed by said elastomeric material.

13. An intervertebral implant for implantation between an upper vertebra and a lower vertebra, the intervertebral implant having a central axis and comprising:
   a first member with a top surface for contacting at least a portion of the upper vertebra and a bottom surface, the first member having a peripheral edge;
   a second member with a top surface and a bottom surface for contacting at least a portion of the lower vertebra, the second member having a peripheral edge;
   an elastomeric material disposed between said bottom surface of said first member and said top surface of said second member, the elastomeric material is a single continuous material extending from and between the peripheral edges of the first and second members and the bottom surface of the first member and the top surface of the second member;
   wherein one of said bottom surface of said first member and said top surface of said second member is provided with first constraint means and the other of said bottom surface of said first member and said top surface of said second member is provided with second constraint means, said first and second constraint means being sized and configured to limit the amount of lateral movement between said first and second members;
   wherein said first and second constraint means are sized and configured such that a gap with a width greater than zero is provided at least transversely to said central axis between said first and second constraint means in an unloaded state;
   wherein said first constraint means is configured as a central pin, having a width, the central pin formed unitary with the first member;
   wherein the second constraint means comprises two separate curved concave protrusions surrounding the first constraint means, the two separate concave protrusions defining two opposite openings, the openings being smaller than the width of the central pin, wherein the two opposite openings allow relative movement of the first and second members in the antero-posterior direction to differ from the amount of relative movement in the lateral direction; and
   wherein said at least two separate curved concave portions are provided with a concavely curved interior wall facing the central axis.

14. The intervertebral implant of claim 13, wherein said elastomeric material extends into said gap.

15. The intervertebral implant of claim 13, further comprising form fitting retention means disposed between said first member and said elastomeric material, and disposed between said second member and said elastomeric material, said retention means comprising a peripheral frame extending from said bottom surface of said first member and said top surface of said second member, said peripheral frame being sized and configured to secure said elastomeric material in-between said first and second members.

16. The intervertebral implant of claim 15, wherein said peripheral frame includes an undercut, the undercut being sized and configured to be encompassed by said elastomeric material.

17. The intervertebral implant of claim 13, wherein the central pin has a convex tip for permitting a tilting motion between said first and second members.

18. An intervertebral implant for implantation between an upper vertebra and a lower vertebra, the intervertebral implant having a central axis and comprising:
   a first member with a top surface for contacting at least a portion of the upper vertebra and a bottom surface, the first member having a peripheral edge;
   a second member with a top surface and a bottom surface for contacting at least a portion of the lower vertebra, the second member having a peripheral edge;
   an elastomeric material disposed between said bottom surface of said first member and said top surface of said second member, the elastomeric material is a single continuous material extending from and between the peripheral edges of the first and second members and the bottom surface of the first member and the top surface of the second member; and
   form fitting retention means disposed between said first member and said elastomeric material, and disposed between said second member and said elastomeric material; wherein said retention means comprises a peripheral frame extending from said bottom surface of said first member and said top surface of said second member, and wherein said peripheral frame further comprises a plurality of holes, wherein the elastomeric material fills through the plurality of holes to connect the elastomeric material to the fitting retention means;

wherein one of said bottom surface of said first member and said top surface of said second member is provided with first constraint means and the other of said bottom surface of said first member and said top surface of said second member is provided with second constraint means, said first and second constraint means being sized and configured to limit the amount of lateral movement between said first and second members;

wherein said first and second constraint means are sized and configured such that a gap with a width greater than zero is provided at least transversely to said central axis between said first and second constraint means in an unloaded state.

19. The intervertebral implant of claim 18, wherein said peripheral frame is provided with an undercut that is encompassed by said elastomeric material.

20. The intervertebral implant of claim 18, wherein said bottom surface of said first member and said top surface of said second member contact said elastomeric material over the entire area of said bottom surface of said first member and said top surface of said second member, and wherein said first and said second members and said elastomeric material form a compact body with planar or convex lateral surfaces.

21. The intervertebral implant of claim 18, wherein said elastomeric material extends into said gap.

22. The intervertebral implant of claim 18, wherein said second constraint means includes first and second curved protrusions.

23. The intervertebral implant of claim 22, wherein said first and second curved protrusions each include a concavely curved interior wall face.

24. The intervertebral implant of claim 18, wherein said first constraint means is configured as a central pin protruding from one of said bottom surface of said first member and said top surface of said second member, said central pin having a convex tip for permitting a tilting motion between said first and second members.

25. The intervertebral implant of claim 24, wherein the central pin has a width and the second constraint means comprises two separate curved concave protrusions surrounding the central pin, the two separate concave protrusions defining two opposite openings, the opening being smaller than the width of the central pin, wherein the two separate concave portions limit relative motion of the first and second members but permit relative movement of the first and second member in the anterior-posterior direction to differ from the amount of relative movement in the lateral direction.

* * * * *